United States Patent [19]
Dill et al.

[11] 4,053,232
[45] * Oct. 11, 1977

[54] ROTATING-COMPENSATOR ELLIPSOMETER

[75] Inventors: Frederick H. Dill, South Salem; Peter S. Hauge, Yorktown Heights, both of N.Y.

[73] Assignee: International Business Machines Corporation, Armonk, N.Y.

[*] Notice: The portion of the term of this patent subsequent to Apr. 29, 1992, has been disclaimed.

[21] Appl. No.: 572,476

[22] Filed: Apr. 28, 1975

Related U.S. Application Data

[63] Continuation-in-part of Ser. No. 373,540, June 25, 1973, Pat. No. 3,880,524.

[51] Int. Cl.² .......................... G01J 4/02; G02F 1/01
[52] U.S. Cl. ................................. 356/118; 250/225
[58] Field of Search ............ 356/114, 115, 117, 118, 356/106 R; 350/12, 13, 14, 15; 250/225

[56] References Cited

U.S. PATENT DOCUMENTS

| | | | |
|---|---|---|---|
| 3,382,761 | 5/1968 | Dyson | 356/106 |
| 3,520,615 | 7/1970 | Smith | 356/106 R |
| 3,594,085 | 7/1971 | Wilmanns | 356/118 |
| 3,741,661 | 6/1973 | Yamanoto et al. | 250/225 |
| 3,880,524 | 4/1975 | Dill et al. | 356/118 |

*Primary Examiner*—Conrad J. Clark
*Attorney, Agent, or Firm*—Sughrue, Rothwell, Mion, Zinn and Macpeak

[57] ABSTRACT

Plane polarized light is reflected from a surface of a sample film to produce an elliptically polarized reflected beam. The reflected beam is passed sequentially through a rotating one-quarter wave plate and a fixed analyzer which transmits a beam whose intensity varies as a function of the rotational angle of the plate. The transmitted beam impinges upon a photodetector which produces an electric signal proportional to the intensity of the transmitted light. The rotating one-quarter wave plate cyclically varies the polarization of the beam, so that the electrical signal, when numerically Fourier analyzed, provides Fourier coefficients having both sin $\Delta$ and cos $\Delta$ terms, where the ellipsometric parameter $\Delta$ is the instantaneous phase difference between the parallel ($R_p$) and perpendicular ($R_s$) components of the electric vector of the elliptically polarized reflected beam; therefore, the phase difference $\Delta$ is uniquely and unambiguously defined in a single measurement. Furthermore, the presence of both sin $\Delta$ and cos $\Delta$ terms permits $\Delta$ to be determined more accurately than is possible with the prior art rotating-analyzer ellipsometer. Since the ellipsometric parameter $\psi$ is also uniquely defined ($\tan\psi = R_p/R_s$), properties of the sample film can be computed. Alternatively, the rotating quarter-wave plate may be placed in the path of the incident plane polarized beam.

5 Claims, 5 Drawing Figures

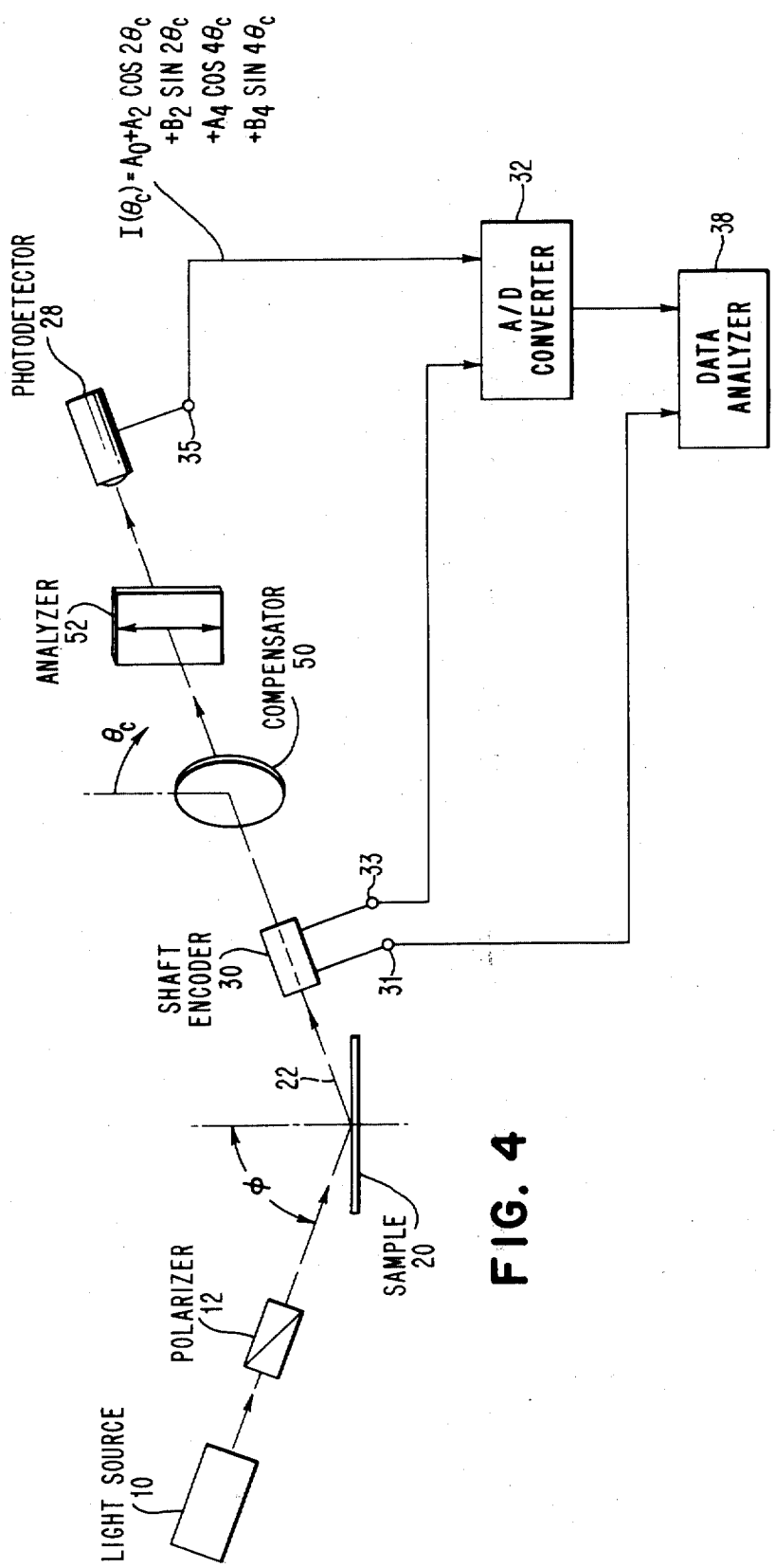

ROTATING-COMPENSATOR ELLIPSOMETER

This application is a continuation-in-part of application Ser. No. 373,540, filed June 25, 1973, now U.S. Pat. No. 3,880,524, assigned to the assignee of the present application, and whose disclosure is expressly incorporated herein by reference.

BACKGROUND OF THE INVENTION

1. Field of the Invention

The invention relates to the field of ellipsometry and, more particularly, to a novel ellipsometer which determines uniquely and unambiguously the phase difference $\Delta$ between the parallel ($R_p$) and perpendicular ($R_s$) components of a beam which has been elliptically polarized by reflection from a sample whose properties are to be measured, while at the same time uniquely determining the ellipsometric parameter $\psi$ of the elliptically polarized beam.

2. Description of the Prior Art

Ellipsometers per se are well known in the prior art. In classical ellipsometry, the beam is passed through two manually adjustable polarizing elements. The polarizing elements are adjusted to produce a null output at a detector upon which the beam impinges. By measuring the relative angular positions of the polarizer elements at which a null is produced, the two ellipsometric parameters $\Delta$ and $\omega$ can be determined, where $\Delta$ is the phase difference between the parallel and perpendicular components $R_p$ and $R_s$, respectively, of the electric vector of the reflected beam, and $\tan \psi = (R_p/R_s)$. From these parameters two unknown properties of the optical system under measurement can be determined, i.e., if the elliptically polarized beam is produced by reflection of a linearly polarized beam from the surface of a film, then the film thickness and refractive index can be determined. If the beam is reflected from a bulk sample, then the complex refractive index of the bulk sample can be determined. In other words, in general, the polarization transfer function of the optical system can be determined.

The outstanding feature of ellipsometry has proven to be the ability to measure the thickness of arbitrarily thin transparent films from which a plane polarized beam is reflected to produce the elliptically polarized beam. However, a disadvantage of the classical manually-adjustable system is that the manual search for the null is a slow process typically requiring a measurement time of 10 minutes; therefore, several methods of automating the measuring procedure have been developed.

One of these automatic ellipsometric systems is disclosed in the above co-pending Application Ser. No. 373,540, filed by us for an Automatic Ellipsometer, on June 25, 1973, now U.S. Pat. No. 3,880,524, and assigned to the assignee of the present application. In this co-pending Application, the second polarizing element or analyzer is rotated continuously, and the intensity of the transmitted light is monitored as a function of the instantaneous rotational angles of the rotating analyzer. From the resulting data, the polarization state of the light can be deduced, and, consequently, the angles $\psi$ and $\Delta$ can be determined by Fourier analysis.

The rotating analyzer technique of said co-pending Application has several desirable features when compared with other approaches to automated ellipsometry. These desirable features include high speed (measurements in 2.0 seconds) and extremely high precision (the polarization azimuth angle $\alpha$ can be measured with a standard deviation of 0.002°). The precision inherent in the rotating analyzer technique derives partly from the use of a Fourier analysis of the measured light intensity data, the Fourier expansion series containing a constant value plus a sinusoidal component of twice the angular rotation frequency of the analyzer. Thus, random noise in the individual determinations of intensity is effectively averaged out over a full rotation of the analyzer, thereby improving measurement precision.

However, as pointed out above, the rotating analyzer technique has a disadvantage in that it is incapable of distinguishing between complementary polarization states of equal orientation and ellipticity but of opposite handedness, i.e., left- or right-handed polarization states that are otherwise equal. This disadvantage manifests itself in an ambiguity in the deduced value of the phase angle $\Delta$, although the angle $\psi$ is determined unambiguously. More specifically, the angle $\psi$ varies only between 0 and 90° and therefore is inherently unambiguous, whereas the ambiguity in the phase angle $\Delta$ occurs because $\Delta$ varies between 0 and 360°.

Of course, this ambiguity in $\Delta$ may be removed when using the rotating analyzer technique either by performing a second measurement after changing the polarization by a known amount, or by knowing a certain amount of prior knowledge of the specimen being measured. However, the necessity of performing a second measurement detracts from the inherent advantage of the speed of the rotating analyzer technique, and, also, the required amount of prior knowledge may not be available.

Even though there exist some particularly basic alternative polarimetric techniques which do not have this disadvantage, they have not been applied to ellipsometry. For example, Clarke and Grainger have categorized all the basic combinations of a retardation plate and linear analyzer as polarimeters, i.e., not as ellipsometers, and shown that one such combination provides a complete determination of polarizaton state by a single measurement; the combination is a rotating retarder in front of a stationary analyzer. See D. Clarke and J. F. Grainger, *Polarized Light and Optical Measurement,* (Pergamon, New York 1971).

SUMMARY OF THE INVENTION

The broad object of the present invention is to provide a novel digital Fourier ellipsometer and ellipsometric method whereby the ellipsometric parameter $\Delta$ may be unambiguously and uniquely determined, where $\Delta$ is the phase angle or difference between the parallel and perpendicular components of a light beam which has been elliptically polarized by reflection.

Another object is to provide an improved automatic ellipsometer which retains all the desirable features of the rotating analyzer ellipsometer described in our aforesaid co-pending Application, but which has the additional capability of unambiguously determining the elliptical polarization phase angle $\Delta$ in a single measurement.

In the apparatus and method for accomplishing these objects, instead of providing a continuously rotating analyzer as disclosed in the aforesaid co-pending Application, the analyzer is fixed, and a quarter-wave retardation element placed in the path of the light beam is continuously rotated. As in said aforesaid co-pending Application, the intensity of the light passing through the analyzer is measured by a photodetector which produces a signal proportional to the impinging light intensity. However, because of the rotating quarter-wave retardation element in the present invention, the photodetector signal contains information which, when numerically Fourier analyzed, permits the phase angle $\Delta$ to be unambiguously and uniquely determined. More specifically, the Fourier coefficients contain both sin $\Delta$ and cos $\Delta$ terms, thereby permitting the sign of the phase angle $\Delta$, i.e., the handedness of the elliptical polarization, to be uniquely determined, whereas in the rotating analyzer ellipsometer, only cos $\Delta$ terms were available, and since $\Delta$ varies between 0° and 360°, the phase angle $\Delta$ could not be uniquely determined without a second measurement. Furthermore, the presence of the sin $\Delta$ term allows more accurate measurement of the magnitude of $\Delta$, especially at values of $\Delta$ where $|\cos \Delta|$ is near unity.

Another object of the invention is to provide a method of calibrating the ellipsometer to account for imperfections in the rotating quarter-wave retardation element.

BRIEF DESCRIPTION OF THE DRAWING

FIG. 4 is a schematic diagram of the essential elements of one embodiment of the improved ellipsometer of this invention.

FIG. 5 is a partial schematic diagram of another embodiment of the improved ellipsometer.

DETAILED DESCRIPTION OF THE PREFERRED EMBODIMENTS

Figure 1:
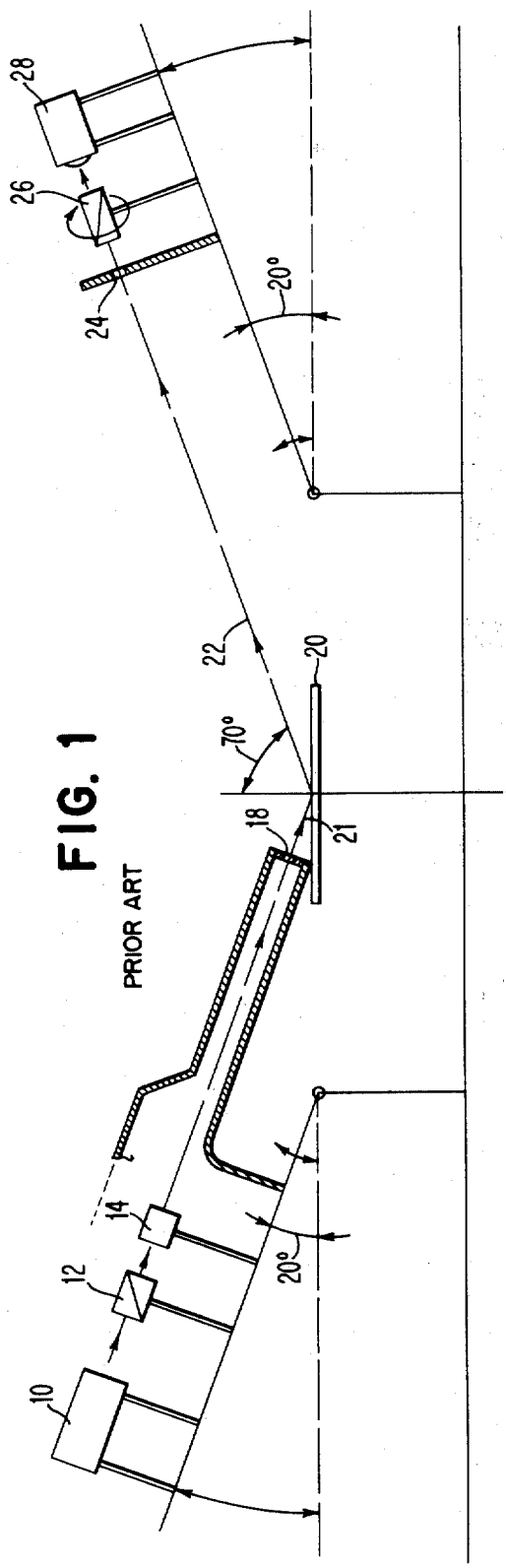
FIG. 1 is a schematic diagram of the mechanical portion of the rotating-analyzer ellipsometer disclosed in co-pending application Ser. No. 373,540.
Figure 3:
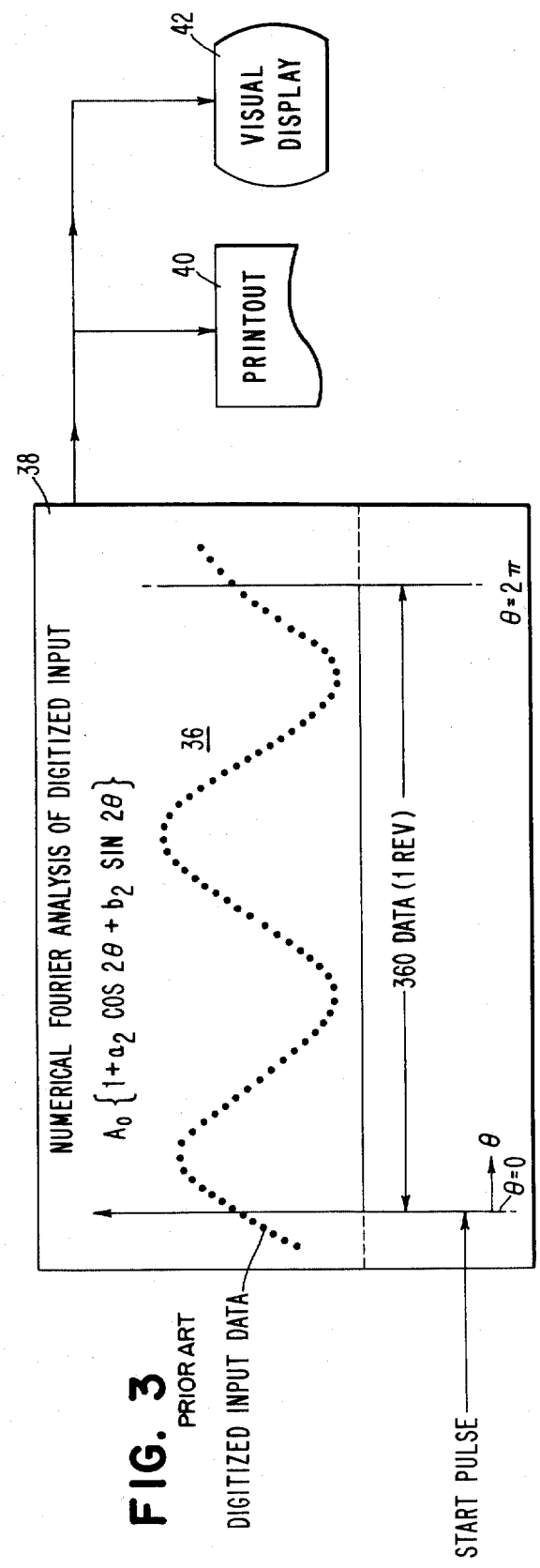
FIG. 3 is a schematic diagram illustrating the data analysis and display functions of the ellipsometer of FIGS. 1 and 2.
Figure 2:
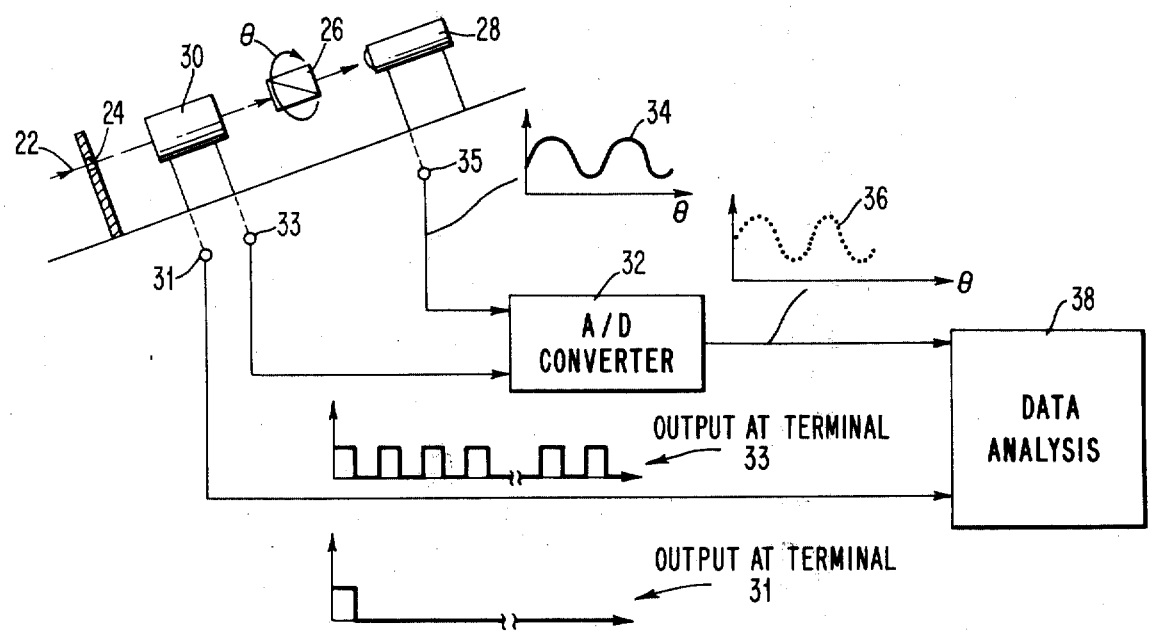
FIG. 2 is a schematic diagram of the electrical portion of the ellipsometer of FIG. 1.

FIGS. 1, 2 and 3 are from our co-pending application Ser. No. 373,540, and are presented for the purpose of providing suitable background for an understanding of the improvement provided by the present invention.

In FIG. 1, a monochromatic light source 10, which may be a 1 mw HeNe laser, produces a light beam which passes through a polarizing prism 12 which is fixed at a known angle (usually about 45°) relative to the plane of incidence of the light beam 21 impinging on the surface of sample 20. The beam also passes through a quarter-wave plate 14 (which is optional and need not be included) and which is also fixed at a known angle, and a spot defining aperture 18. The reflected beam 22 is elliptically polarized and passes through a beam defining aperture 24 and a continuously driven (e.g., at 5 rotations/sec.) spinning polarizing prism (analyzer) 26, and the light from analyzer 26 is detected by a linear light-sensitive device 28, such as a photomultiplier tube.

FIG. 2 shows in more detail the electrical portion of the ellipsometer of FIG. 1. In addition to the elements already shown in FIG. 1, there is shown in FIG. 2 an angular encoder 30 associated with the spinning analyzer 26 and having two output terminals 31 and 33. In actual construction, the encoder 30 is mounted on the hollow shaft which rotates the analyzer 26. The output 31 provides a single trigger pulse for each revolution of the analyzer 26, and the terminal 33 provides a pulse for each of a plurality of small equal fractions of each revolution of the analyzer. The pulses appearing at terminal 33 are applied as triggers to an analog-to-digital converter 32.

The output terminal 35 of the photomultiplier 28 is connected as the analog input of the analog-to-digital converter 32, the output signal of the photomultiplier 28 generally taking the form of the waveform designated by the numeral 34. Converter 34 converts the analog input from the photomultiplier to a discrete digitized output which generally takes the form depicted by the dotted waveform designated by the numeral 36. The digital output of the converter 32 is applied to a data analyzer stage 38 which may suitably be a small computer, such as the IBM 1130, manufactured by the IBM Corporation, or by any other small digital computer. In the data analyzer 38, the data is numerically Fourier analyzed to determine the Fourier coefficients, since it is only these coefficients which are needed in the ellipsometric analysis of the reflected light and not the full Fourier transform. Once the normalized second harmonic coefficients of the Fourier transform have been ascertained, standard ellipsometric formulae are evaluated to find whatever calculable parameters characterizing the optical properties of the sample are desired. The values of these parameters are typed out on a printout, such as a typewriter, or visually displayed in some manner, such as by means of a storage cathode ray tube, Nixie tubes, and the like.

More specifically, in FIG. 3, the data analyzer 38 is depicted as performing the numerical Fourier analysis of the digitized input waveform 36. In the case of the rotating analyzer ellipsometer of said co-pending Application, the normalized coefficients $a_2$, $b_2$ of the Fourier series are determined. The standard ellipsometric formulae are evaluated to obtain desired sample parameters, such as film thickness and refractive index. Also, in FIG. 3, there are shown a printout stage 40 and a visual display stage 42. The information which is printed or displayed is azimuth $\alpha$, ellipticity $\chi$, the ellipsometric parameters $\psi$ and $\Delta$, film thickness, refractive index, etc. To effect the Fourier analysis in data analyzer stage 38, i.e., the computer, there may be employed the programs designated "System/7 Fast Fourier Transform Program RPQ P82000", described in "IBM INSTALLATION NEWSLETTER", issue No. 72-11, dated June 2, 1972 and published by the IBM Corporation.

Also shown in the co-pending Application and cited here for background, is a means for mounting the polarizing element 12 so that the angle of the polarizing element relative to the plane of incidence may be st at selected angles, such as 0°, 12°, 45° and 90°.

FIG. 4 is a schematic diagram illustrating the improved ellipsometer of this invention. For ease of understanding the invention relative to the above description with respect to the rotating-analyzer ellipsometer illustrated in FIGS. 1, 2 and 3, those elements of FIG. 4 which are the same as corresponding elements in FIGS. 1 and 2 bear the same reference numerals as those used in FIGS. 2 and 3. Thus, a monochromatic light source 10 directs a light beam 21 through a fixed polarizer 12 so that the beam is incident on the surface of the sample 20 at an angle of incidence $\phi$. Of course, as with the rotating-analyzer ellipsometer of the co-pending application Ser. No. 373,540, the polarizer 12 may be mounted so that its azimuth may be adjusted to be set at different discrete predetermined angles relative to the plane of incidence. The reflected beam is then passed through a rotating quarter-wave optical retarder or compensator 50, such as a quarter-wave plate. The compensator is rotated at a constant angular velocity by a suitable driving shaft (not shown), for example. The instantaneous rotational angle of the compensator is designated $\theta_c$. The light passing through the compensator is directed to a fixed analyzer 52, and the light transmitted by the analyzer impinges upon a photodetector 28 which produces at terminal 35, an electric analog signal which is a function of the intensity of the light transmitted by analyzer 52.

For ease of understanding the invention, the following combination of optical component azimuths appears to yield the simplest form of the acquired intensity data. The polarizer 12 is set at an angle of 45° with respect to the plane of incidence, and the fixed analyzer 52 is set at an angle of 0°. Furthermore, assuming that the fast axis of the compensator 50 is at an instantaneous angle $\theta_c$ with respect to the plane of incidence, and further assuming for the moment that the compensator is ideal, i.e., has a retardation of exactly one-quarter wave length, the intensity I ($\theta_c$) of the light impinging on the photodetector 28 has the following form to within a multiplicative constant:

$$I(\theta_c) = A_0 + A_2 \cos 2\theta_c + B_2 \sin 2\theta_c + A_4 \cos 4\theta_c + B_4 \sin 4\theta_c \quad (1)$$

where the Fourier coefficients indicated in equation (1) have the form:

$A_0 = 2 - \cos 2\psi$ $A_2 = 0$ $B_2 = 2 \sin 2\psi \sin \Delta$ $A_4 = -\cos 2\psi$ $B_4 = \sin 2\psi \cos \Delta$ Since intensity is measured only to within a multiplicative constant, it is only the ratios of the above Fourier coefficients that contain the desired information regarding the sample parameters $\psi$ and $\Delta$. Therefore, it is most convenient to divide each coefficient by the average intensity level $A_0$, thereby obtaining:

$a_2 = A_2/A_0 = 0 \quad (2)$ $b_2 = B_2/A_0 = 2 \sin 2\psi \sin \Delta/(2-\cos 2\psi) \quad (3)$ $a_4 = A_4/A_0 = -\cos 2\psi/(2-\cos 2\psi) \quad (4)$ $b_4 = B_4/A_0 = \sin 2\psi \cos\Delta/(2-\cos 2\psi) \quad (5)$ Equations 4 and 5 may be solved for $\psi$ and $\Delta$ as follows:

$$\psi = \tfrac{1}{2} \cos^{-1}\left(\frac{2a_4}{a_4 - 1}\right) \quad (6)$$

$$\Delta = \cos^{-1}\left(\frac{-b_4}{a_4 \tan 2\psi}\right) \quad (7)$$

From the above equations, it will be described how the measurement of the intensity of the light transmitted by the combination of the rotating compensator 50 and the fixed analyzer 52 as a function of the compensator azimuth $\theta_c$ allows a completely unambiguous determination of the polarization state of the incident light, and thus an unambiguous determination of the sample parameters $\psi$ and $\Delta$ for the purpose of ellipsometry. The added information to remove the ambiguity comes about by virtue of the fact that the intensity I ($\theta_c$) is now a constant value plus two sinusoidal terms, as contrasted to the single sinusoidal term obtained in the rotating analyzer ellipsometer, as indicated in FIG. 3. Referring to equation 1 above, it is seen that one of these sinusoidal components ($B_4 \sin 4\theta_c$) contains four times the compensator angular frequency, thereby yielding essentially the same information as obtained in the data derived in the rotating analyzer ellipsometer, and sinusoidal terms ($A_2 \cos 2\theta_c$) and ($B_2 \sin 2\theta_c$) containing double the angular frequency. It is noted that the latter term changes phase by 180° with a change in handedness of the polarization of the incident light. Thus, the numerical Fourier analysis technique employed in the rotating-compensator ellipsometer is clearly applicable to analysis of the intensity data I ($\theta_c$) obtained in the rotating-compensator ellipsometer of FIG. 4.

This advantage of the improved ellipsometer of this invention may also be seen with respect to the mathematical expressions set forth in equations (2) through (7). It can be seen that $\psi$ is determined uniquely since it always lies between 0° and 90°, but $\Delta$ can be either of two values since it lies between 0° and 360°. However, in the improved ellipsometer of the present invention, the correct value of $\Delta$ may be determined because of the added information contained in the $b_2$ term, since by inspection it must have the same numerical sign as sin $\Delta$. Furthermore, since the two possible values of $\Delta$ permitted by equation (7) give opposite signs to the value of $b_2$, the ambiguity in the sign of $\Delta$ is removed, and thus, $\Delta$ is uniquely and unambiguously determined.

Returning to FIG. 4, the shaft encoder 30 provides the same function as in the rotating-analyzer ellipsometer 30 shown in FIG. 2. However, in FIG. 4, the shaft encoder 30 is suitably driven by the same shaft which rotates the compensator 50, and the timing pulses produced on terminals 31 and 33 correspond to the rotation of the compensator 50, rather than that of the rotating analyzer 26 of FIGS. 1 and 2. The intensity signal from the output of photodetector 28 is again digitized in the analog-to-digital converter 32 and then numerically Fourier analyzed in the data analyzer 38 to determine the values of $\Delta$ and $\psi$ in the same manner as described in the aforesaid co-pending Application.

FIG. 5 illustrates another embodiment of the invention which is identical to the embodiment illustrated in FIG. 4, with the exception that the rotating compensator 50 is located in the path of the incident beam between the polarizer 12 and the sample 20. The same result is obtained for the configuration of FIG. 5, but in the mathematical calculations the azimuth angles of the polarizer 12 and analyzer 52 are reversed with respect to the analysis for the configuration of FIG. 4.

For the above calculations, an ideal compensator was assumed. However, in practice, compensators have a retardance which is only approximately a quarter of a wavelength for all wavelengths of interest, and in addition, they exhibit a slight difference in transmission along their two principal axes. In classical ellipsometry, these imperfections necessitate the performing of two manual null measurements to account for the non-ideal compensators. However, as explained below, the present rotating-compensator ellipsometer may be calibrated to compensate for these imperfections.

These imperfections of the compensator affect the measured data as follows. Let the complex transmittance ratio of the slow and fast orientations of the compensator be described by the two compensator parameters $\psi_c$ and $\Delta_c$ (remembering that $\psi$ and $\Delta$ are sample parameters) as follows:

$$T_{slow}/T_{fast} = \tan \psi_c e^{-i\Delta_c} \quad (8)$$

where ideally $\psi_c = 45°$, and $\Delta_c = 90°$. Then the coefficients of equation (1) become:

$$A_0 = 2 - (1 + \sin 2\psi_c \cos\Delta_c) \cos 2\psi$$

$$A_2 = 2 \cos 2\psi_c (1 - \cos 2\psi)$$

$$B_2 = 2 \sin 2\psi(\cos 2\psi_c \cos\Delta + \sin 2\psi_c \sin\Delta_c \sin\Delta)$$

$$A_4 = -(1 - \sin 2\psi_c \cos\Delta_c) \cos 2\psi$$

$$B_4 = (1 - \sin 2\psi_c \cos\Delta_c) \sin 2\psi \cos\Delta$$

The effect of the compensator imperfections may be removed by first characterizing the compensator to determine the corresponding values of $\psi_c$ and $\Delta_c$. This can be done by performing a measurement in which the light from the polarizer 12 in FIG. 4, for example, is aimed directly into the rotating compensator 50 without being reflected from the sample, such an arrangement being optically equivalent to setting $\psi = 45°$ and $\Delta = 0°$ in the equations immediately above, so that the resulting coefficients for the calibration measurement are of the form:

$$a_2 = A_2/A_0 = \cos 2\psi_c \quad (9)$$

$$b_2 = B_2/A_0 = \cos 2\psi_c \quad (10)$$

$$a_4 = A_4/A_0 = 0 \quad (11)$$

$$b_4 = B_4/A_0 = (1 - \sin 2\psi_c \cos\Delta_c)/2 \quad (12)$$

Solving for the compensator parameters, one obtains:

$$\psi_c = \tfrac{1}{2} \cos^{-1}(a_2) \text{ (should be approximately 45°)} \quad (13)$$

$$\Delta_c = \cos^{-1}((1-2b_4)/\sin 2\psi_c) \text{ (should be approximately 90°)} \quad (14)$$

There is also an experimental check on this measurement, namely that $a_2$ should be equal to $b_2$, and that $a_4$ should be zero. With the compensator thus characterized or calibrated, we may determine the sample parameters for the imperfect compensator by solving:

$$\psi = \tfrac{1}{2} \cos^{-1}(2a_4/\alpha a_4 - \delta)) \quad (15)$$

$$\Delta = \cos^{-1}(-b_4/(a_4 \tan 2\psi)) \quad (16)$$

where $$\alpha = 1 + \sin 2 \psi_c \cos \Delta_c \quad (17)$$

$$\delta = 1 - \sin 2 \psi_c \cos \Delta_c$$

Therefore, the correct or compensated value for $\Delta$ of the two values allowed by equation (16) may be determined as before from the values of $b_2$. Note that equation (16) is identical to equation (7), showing that compensator imperfections affect only the value of the sample parameter $\psi$.

As should be clear from the foregoing, the use of Fourier analysis of intensity versus compensator azimuth data as employed in the rotating-analyzer ellipsometer data of the aforesaid co-pending Application provides a fast and unique determination of the sample parameters $\psi$ and $\Delta$, while removing the inherent ambiguity in the value of $\Delta$ determined by the rotating-analyzer ellipsometer, and does so without any sacifice in speed. Furthermore, the present rotating-compensator ellipsometer, because of the generation of the sin $\Delta$ term, provides more accurate determination of the value of $\Delta$, especially when the value of cos $\Delta$ approaches unity. In addition, the effects of non-ideal compensators are taken into account exactly by the present rotating-compensator ellipsometer, without the approximating assumption that the compensator is ideal.

In the foregoing disclosure, the symbols $R_p$ and $R_s$ have been applied respectively to the parallel and perpendicular components of the electric vector of the elliptically polarized reflected light beam. Further, the ellipsometric parameters of the sample ($\chi$ and $\Delta$) have been defined in terms of the aforesaid symbols $R_p$, $R_s$. The specific case of plane polarized incident light oriented 45 degrees from the plane of incidence is tacitly assumed by the above usage of the terms $R_p$ and $R_s$. However, the disclosure relates to the most general case of elliptically polarized incident and reflected light. In this case, the following definitions hold:

$$R_p = E_p^r/E_p^i$$

$$R_s = E_s^r/E_s^i$$

where $E_p^i$ and $E_s^i$ are respectively the parallel and perpendicular components of the elliptically polarized incident light beam, and $E_p^r$ and $E_s^r$ are respectively the parallel and perpendicular components of the elliptically polarized reflected light beam. $R_p$ and $R_s$ are thus respectively the reflection coefficients of the sample for parallel and perpendicularly polarized light. The ellipsometric sample parameters $\psi$ and $\Delta$ are related to $R_p$ and $R_s$ by the following relationship:

$$R_p/R_s = \tan \psi \, e^{i\Delta}.$$

Thus in the general case mentioned above, $\Delta$ is the phase difference between the parallel ($R_p$) and perpendicular ($R_s$) reflection coefficients of the sample, and $\psi$ is defined as $$\tan \psi = |(R_p/R_s)|$$

where the vertical bars denote the absolute value of complex ratio $R_p/R_s$. The invention allows a complete and unambiguous determination of $\psi$ and $\Delta$ for the general case of elliptically polarized incident and reflected light.

We claim:

1. In an automatic ellipsometer for measuring characteristics of a sample and including:
    a monochromatic light source for directing a light beam of a known wavelength onto said sample at a known angle of incidence so that the beam is reflected from the surface of the sample;
    a first polarizing element in the path of incident light beam and adapted to be fixed at a predetermined angle relative to the plane of incidence of the beam;
    adjusting means for setting the azimuth of said first polarizing element at different discrete predetermined angles relative to said plane of incidence;
    a second polarizing element disposed in the path of the reflected light beam;
    a photoresponsive device in the path of said reflected light beam and responsive to said beam, after it has passed through said second polarizing element, to produce an electrical signal which is a function of the intensity of the reflected light beam;
    an angular encoder;
    an analog-to-digital converter; and
    a data analyzing means;

the improvement comprising:
a rotating optical compensator disposed in the path of the light beam;
said second polarizing element being fixed at a known angle relative to said plane of incidence;
said angular encoder being associated with said rotating compensator for providing outputs consisting of first pulses for each revolution of said rotating compensator and respective second pulses for each chosen fraction of each of the revolutions;
said analog-to-digital converter being responsive to the outputs of said angular encoder and to the signal from said photoresponsive device for digitizing said signal in accordance with said second pulses; and
said data analyzing means being responsive to the digitized signal from said analog-to-digital converter and to said first pulses for analyzing the digitized signal.

2. The improvement as defined in claim 1 wherein said rotating optical compensator comprises a rotating quarter-wave plate.

3. The improvement as defined in claim 1 wherein said optical compensator is disposed in the path of the incident light beam between said first polarizing element and the sample.

4. The improvement as defined in claim 1 wherein said optical compensator is disposed in the path of the reflected light beam between the sample and said fixed polarizing element.

5. The improvement as defined in claim 1 wherein: said first polarizing element plane-polarizes the incident light beam; the rotating optical compensator cyclically varies the polarization of the light beam; and the light beam reflected from the sample is elliptically polarized, so that said signal contains information, which, when numerically Fourier analyzed, produces Fourier coefficients having both $\sin \Delta$ and $\cos \Delta$ terms, whereby $\Delta$ is uniquely and unambiguously determined, $\Delta$ being the phase difference between the parallel and perpendicular components of the electric vector of the beam reflected from the sample; and said data analyzing means comprises digital computer means for numerically Fourier analyzing said signal from said photoresponsive device and for unambiguously computing both the phase difference $\Delta$ and the angle $\psi$, where $\tan \psi = R_p/R_s$, and, $R_p$ and $R_s$ are the magnitudes of the parallel and perpendicular components, respectively, of the electric vector of the reflected beam.

* * * * *